United States Patent [19]

D'Silva

[11] 4,264,625
[45] Apr. 28, 1981

[54] PESTICIDAL UNSYMMETRICAL BIS-ARYLCARBAMATE SULFIDE COMPOUNDS

[75] Inventor: Themistocles D. J. D'Silva, South Charleston, W. Va.

[73] Assignee: Union Carbide Corporation, New York, N.Y.

[21] Appl. No.: 954,867

[22] Filed: Oct. 26, 1978

Related U.S. Application Data

[63] Continuation-in-part of Ser. No. 801,331, May 27, 1977, abandoned.

[51] Int. Cl.³ .................. A01N 47/24; C07D 125/075
[52] U.S. Cl. ................................. 424/300; 424/276; 424/277; 424/278; 424/282; 424/283; 424/285; 260/340.3; 260/340.5 R; 260/340.7; 260/340.9 R; 260/346.73; 260/465 R; 549/21; 549/29; 549/36; 549/51; 560/133; 560/134; 560/135; 560/136; 560/137

[58] Field of Search .................. 260/327 M, 332.2 R, 260/340.3, 340.5 R, 340.7, 340.9 R, 346.73, 465 D; 560/133, 134, 135, 136, 137; 424/276, 277, 278, 282, 283, 285, 300; 549/21, 29, 36, 51

[56] References Cited

U.S. PATENT DOCUMENTS

| | | | |
|---|---|---|---|
| 4,124,721 | 11/1978 | D'Silva | 260/346.73 |
| 4,181,734 | 1/1980 | D'Silva | 260/346.73 |

FOREIGN PATENT DOCUMENTS 2131399  12/1972  Fed. Rep. of Germany .

Primary Examiner—Henry R. Jiles
Assistant Examiner—Bernard Dentz
Attorney, Agent, or Firm—William R. Moran; Dale Lynn Carlson

[57] ABSTRACT

Bis-[N-Alkyl-N-arylcarbamate] sulfide compounds exhibit outstanding miticidal and insecticidal activity, coupled with substantially reduced mammalian toxicity, and phytotoxicity.

21 Claims, No Drawings

PESTICIDAL UNSYMMETRICAL BIS-ARYLCARBAMATE SULFIDE COMPOUNDS

This application is a Continuation-In-Part of my co-pending U.S. patent application Ser. No. 801,331, filed May 27, 1977, now abandoned.

This invention relates to N-substituted bis-arylcarbamate sulfide compounds and to methods for preparing the same. This invention is also directed to insecticidal and miticidal compositions comprising an acceptable carrier and an insecticidally and miticidally effective amount of a compound of controlling insects, mites and nematodes by subjecting them to an insecticidally or miticidally effective amount of a compound of this invention.

More particularly, this invention relates to compounds of the formula:

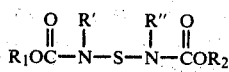

$$R_1OC(=O)-N(R')-S-N(R'')-C(=O)OR_2$$

wherein:

R' and R'' are the same or different and are alkyl having from 1 to 4 carbon atoms;

$R_1$ is:

(A) naphthyl, tetrahydronaphthyl, benzofuranyl, benzodioxanyl, dihydrobenzofuranyl, indanyl, benzothienyl, or benzodioxalanyl all of which may be either unsubstituted or substituted with one or more alkyl groups; or (B) phenyl either unsubstituted or substituted with one or more alkyl, alkoxy, alkylthio, dialkylaminomethyleneimino, dialkylamino, methylenedioxy, halo, nitro, cyano, alkynyloxy, phenoxy, alkenyl, alkynyl, dialkylformamidino, alkylsulfonylalkyl, alkylsulfinylalkyl, alkoxycarbonylamino, alkylthioalkyl, trihalomethyl 2-dioxalanyl, 2-dioxanyl, 2-dithianyl, 2-dithiolanyl or 2-oxathiolanyl group;

$R_2$ is:

(A) alkylphenyl having from nine to twenty aliphatic carbon atoms;

(B) phenyl, alkoxyphenyl or alkylphenyl all of which are substituted with one or more alkynyloxy, alkynyl, phenoxy, alkenyl, alkoxycarbonylamino, trihalomethyl, alkylthioalkyl, alkylsulfonylalkyl, alkylsulfinylalkyl, dialkylformamidino, dialkylaminomethyleneamino, methylenedioxy, cyano, dicyanoethylene, 2-dioxalanyl, 2-dithianyl, 2-dioxanyl, 2-dithiolanyl or 2-oxathiolanyl groups;

with the proviso that $R_1$ and $R_2$ substituents individually may not include more than twenty aliphatic carbon atoms, except as noted and that when $R_1$ is unsubstituted or substituted dihydrobenzofuranyl, $R_2$ is other than alkyl phenyl or substituted phenyl, alkoxyphenyl or alkylphenyl wherein the substituents are alkylthioalkyl, alkylsulfonylalkyl or alkylsulfinylalkyl.

The formamidino and the dialkylamino substituents can also be in the form salts of organic or inorganic acid, as for example, the oxalate, citrate, acetate, propionate, chloride, phosphate, nitrate, sulfonate, sulfate or formate salt.

The following miticidally and insecticidally active compounds are illustrative of the compound of this invention all of which can be conveniently prepared by the process of this invention simply by selecting appropriate starting materials for use in the procedures described below:

N-[1-Naphthyl methylcarbamate]N-[4-hexdecyl phenyl methylcarbamate] sulfide.

N-[1-Naphthylmethylcarbamate] N-[4-methylthio-3,5-xylyl methylcarbamate]sulfide

N-[1-Naphthylmethylcarbamate] N-[2-ethylthiomethylphenylmethylcarbamate]sulfide

N-[1-Naphthylmethylcarbamate] N-[4-dimethylaminomethyleneimino-3,5-xylyl methylcarbamate]sulfide N-[1-Naphthyl methylcarbamate] N-[4-dimethylaminomethyleneimino-3-isopropylphenyl methylcarbamate] sulfide, hydrochloride N-[1-Naphthyl methylcarbamate] N-[4-(2,2-dicyanoethenylene) 2,6-di-tert-butylphenyl methylcarbamate] sulfide N-[2-Methyl-2,3-dihydro-7-benzofuranyl methylcarbamate] N-[3-trifluoromethylphenyl methylcarbamate] sulfide N-[1-Naphthyl methylcarbamate] N-[3-dimethylaminomethyleneiminophenyl methylcarbamate] sulfide hydrochloride N-[2,2-Dimethyl-2,3-dihydro-7-benzofuranyl methylcarbamate] N-[4-(dimethylaminomethyleneimino)-3-methylphenyl methylcarbamate]-sulfide hydrochloride N-[2-(1,3-Oxathiolan-2-yl)phenyl methylcarbamate] N-[3-ethynylphenyl methylcarbamate]sulfide N-[2-(1,3-Dioxolan-2-yl)phenyl methylcarbamate] N-[4-cyanophenyl methylcarbamate]sulfide N-[3,4-Methylenedioxyphenyl methylcarbamate] N-[2-cyclopropylphenyl methylcarbamate]sulfide N-[2-Isopropylphenyl methylcarbamate] N-[3-phenoxyphenyl methylcarbamate]sulfide N-[1-Naphthyl methylcarbamate] N-[2-(dithiolan-2-yl)phenyl methylcarbamate]sulfide N-[1-Naphthyl methylcarbamate] N-[4-dodecylphenyl methylcarbamate] sulfide N-[1-Naphthyl butyl carbamate] N-[2-(oxathiolan-2-yl)phenyl butylcarbamate]sulfide N,N'-Thio-bis-(2-(1,3-oxathiolan-2-yl)phenyl methylcarbamate).

N,N'-Thio-bis-(3-proynyloxyphenyl methylcarbamate).

N,N'-Thio-bis-(2-(1-methylpropynyloxy)phenyl methylcarbamate).

N,N'-Thio-bis-(2-(2-butynyloxy)phenyl methylcarbamate).

N,N'-Thio-bis-(4-methoxycarbonylamino-3,5-xylyl methylcarbamate).

N,N'-Thio-bis-(3-phenoxyphenyl methylcarbamate).

N,N'-Thio-bis-(4-dimethylaminomethyleneimino-3-isopropylphenyl methylcarbamate).

N,N'-Thio-bis-(3-dimethylaminomethyleneiminophenyl methylcarbamate)hydrochloride.

N,N'-Thio-bis-(2-ethylthiomethylphenyl methylcarbamate).

N,N'-Thio-bis-(2-ethylsulfonylmethylphenyl methylcarbamate).

All of the compounds within the purview of the generic formula set forth above exhibit miticidal and insecticidal activity to a lesser or greater extent. Accordingly, these compounds are extremely useful for the control of insect, nematode and mite pests. Some of these compounds exhibit very high levels of miticidal, nematocidal and insecticidal activity in extremely small dosages while others require larger dosages to be effective.

In general, the compounds of this invention are either totally lacking in phytotoxicity or exhibit only minimal phytotoxicity with respect to economically important crop species. In addition, these compounds exhibit substantially reduced levels of mammalian toxicity as compared to known pesticidal compounds having a comparable spectrum of activity against insect, arachnid and nematode pests.

Preferred because of their higher levels of miticidal and insecticidal activity are the compounds of this invention in which:

R' and R" are methyl;

$R_1$ is naphthyl, or phenyl substituted with one or more alkoxy, alkyl, phenoxy, alkenyl, alkynyloxy, 2-dithiolanyl, 2-oxathiolanyl, 2-dithianyl, alkylthio, halo, dialkylamino, alkoxycarbonylamino, or dialkylformamidino groups.

$R_2$ is alkylphenyl having from 9 to 16 aliphatic carbon atoms.

The bis-[N-alkyl-N-arylcarbamate] sulfide compounds of this invention can be conveniently prepared by a variety of methods. Two preferred methods are illustrated by the reaction scheme set forth below in which R', R", $R_1$ and $R_2$ are as described above, except as noted:

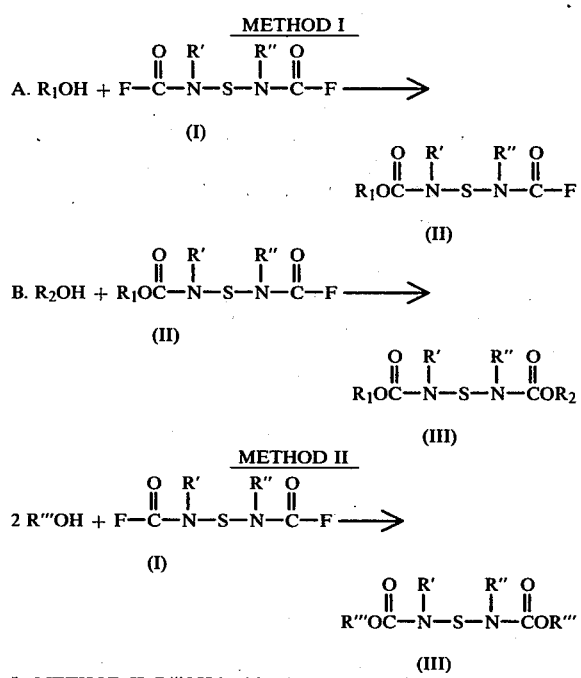

In METHOD II, R'''OH is either $R_1$OH or $R_2$OH.

METHOD I is a two-step reaction sequence which can be conducted in-situ or the carbamate-sulfenyl carbamoyl halide intermediate (II) of Step A can be isolated and used as the reactant of Step B at some later time. In Step A, one equivalent of an appropriately substituted hydroxyl reactant, either $R_1$OH or $R_2$OH, is reacted with one equivalent of the bis-(N-alkyl-N-fluorocarbonylamino) sulfide reactant (I), in presence of at least one equivalent of an acid acceptor, preferably in an aprotic solvent to yield the intermediate carbamate sulfenyl carbamoyl halide (II). In Step B, an equivalent of the intermediate carbamate-sulfenyl carbamoyl halide (II) reactant is then reacted with a second equivalent of a hydroxyl reactant, $R_2$OH if $R_1$OH was used as the reactant in Step A or $R_1$OH if $R_2$OH was used as the reactant of Step A. Step B is also conducted in the presence of at least one equivalent of an appropriate acid acceptor and in an aprotic solvent, to yield the desired bis-arylcarbamate compound (III).

In the procedure illustrated in METHOD II, two equivalents of an appropriately substituted hydroxyl reactant are reacted with one equivalent of the bis-(N-alkyl-N-fluorocarbonylamino) sulfide reactant (I) in an appropriate solvent in the presence of at least two equivalents of an acid acceptor.

The reactions of METHODS I and II are normally conducted in an aprotic organic solvent. Illustrative of aprotic organic solvents which are suitable as reaction solvents in the practice of the preferred embodiments of this invention are saturated and unsaturated aliphatic and aromatic hydrocarbons, e.g. hexane, cyclohexane, octane, dodecane, naphtha, decalin, kerosene, tetrahydronaphthalene, cycloheptane, alkylcycloalkane, benzene, toluene, xylene, naphthalene, alkylnaphthalene, or the like, ethers such as tetrahydrofuran, tetrahydropyran, diethyl ether, dioxane, 1,2-dimethoxybenzene, 1,2-ethoxybenzene, the dialkyl ethers of ethylene glycol, of dipropylene glycol, of butylene glycol, or diethylene glycol, of dipropylene glycol, or chlorinated aliphatic hydrocarbons as for example, chloroform, dichloromethane, methylene dichloride, 1,1-dichloroethane, carbon tetrachloride or the like.

The acid acceptor utilized in the conduct of the reactions of METHODS I and II may be either an organic or inorganic base. Illustrative of organic bases that are useful as acid acceptors are tertiary amines, alkali metal alkoxides or the like. Bases such as sodium hydroxide, potassium hydroxide or the like are illustrative of inorganic bases which are useful in the conduct of this reaction. Preferred acid acceptors are aromatic and aliphatic tertiary amines, such as triethylamine, pyridine, trimethylamine, 1,4-diazobicyclo [2.2.2] octane and the like.

When an inorganic base is used as the acid acceptor, phase transfer agents may be used to facilitate the transfer of the acid acceptor across the organic/inorganic phase interface. Illustrative of useful phase transfer agents are crown ether compounds, quaternary ammonium halide compounds or the like.

In these reactions, the reaction temperature is not critical and can be varied over a wide range. The reaction is preferably conducted at a temperature of from about −30° C. and upwards to approximately 130° C. Particularly preferred reaction temperatures are from about 0° C. to about 75° C.

Reaction pressures are not critical. The process can be conducted at either subatmospheric, atmospheric or superatmospheric pressure. For convenience the reaction is usually conducted at atmospheric or autogeneous pressure.

Hydroxylated aryl compounds employed as reactants in the reactions of METHODS I and II are well known compounds that can be prepared by well known synthetic procedures or obtained from commercial sources.

The bis-(N-alkyl-N-fluorocarbonylamino)sulfide precursors can be conveniently prepared by reacting sulfur dichloride with N-alkylcarbamoyl fluoride in toluene in the presence of an acid acceptor as for example triethylamine or pyridine. This procedure is described in more detail in U.S. Pat. No. 3,639,471.

The following specific examples are presented to particularly illustrate the invention:

EXAMPLE I

Preparation of
Bis-(N-Methyl-N-fluorocarbonylamino)sulfide

To a polyethylene reactor containing 80 g (4.0 m) of hydrogen fluoride in 1800 ml of toluene, cooled to −40° C. was added dropwise with stirring 228 g (4.0 m) of methyl isocyanate, over a period of 20 min. The reaction mixture was allowed to warm to 0° C. and was maintained at this temperature for 1 hr. Then 206 g (2.0 m) of freshly distilled sulfur dichloride was added followed by a slow addition of 346 g (4.4 m) of pyridine at −20° to 0° C. After stirring for 2 hrs. at −10° C. and for 16 hrs. at ambient temperature, the reaction mixture was diluted with 500 ml of water. The toluene layer was further washed 3 times with 500 ml of water, dried and distilled to afford 244 g (66 percent) of preparation of Bis-(N-Methyl-N-fluorocarbonylamino)sulfide. B.p. 55°–57° C./0.25 mm. On standing the distillate crystallized. m.p. 40°–41° C.

Calc'd for $C_4H_6F_2N_2O_2S$: C, 26.09; H, 3.28; N, 15.21. Found: C, 26.19; H, 3.20; N, 14.79.

EXAMPLE II

Preparation of
2,2-Dimethyl-2,3-dihydro-7-[N-methyl-N-(N'-methyl-N'-fluorocarbonylaminosulfenyl)carbamoyloxy]benzofuran To a solution of 5.0 g of bis-(N-methyl-N-fluorocarbonylamino)sulfide, prepared as in Example I, and 5.0 g of 2,2-dimethyl-2,3-dihydrobenzofuran-7-ol in 75 ml of dioxane, was added 4.0 g of triethylamine. After allowing the reaction mixture to stand at ambient temperature for 6 days, it was diluted with 200 ml of water and extracted in ethyl acetate. The ethylacetate extract was washed with water, dried and concentrated under vacuo. Purification by silica gel chromatography afforded 5.0 g of 2,2-Dimethyl-2,3-dihydro-7-[N-methyl-N-(N'-methyl-N'-fluorocarbonylaminosulfenyl)carbamoyloxy]benzofuran as a viscous oil.

Calc'd for $C_{14}H_{17}FN_2O_4S$: C, 51.21; H, 5.21; N, 8.53. Found: C, 51.90; H, 5.34; N, 8.60.

EXAMPLE III

Preparation of
1-[N-Methyl-N-(N'-methyl-N'-fluoroformylaminosulfenyl)carbamoyloxy]naphthalene To a solution of 4.32 g of 1-naphthol in 25 ml of dioxane was added 6.0 g of bis-(N-methyl-N-fluorocarbonylamino)sulfide, prepared as in Example I. To this solution was added dropwise with stirring 3.03 g of triethylamine diluted with 5.0 ml of dioxane. After stirring for 28 hrs. at room temperature the solution was concentrated under reduced pressure and then taken in ethyl acetate, washed with water, dried over magnesium sulfate and concentrated to 7.22 g of an oil. The 1-[N-Methyl-N-(N'-methyl-N'-fluoroformylaminosulfenyl)carbamoyloxy] naphthalene crystallized from isopropyl ether, m.p. 58°–60° C.

Calc'd for $C_{14}H_{13}FN_2O_3S$: C, 54.53; H, 4.25; N, 9.09. Found: C, 54.58; H, 4.32; N, 8.96.

EXAMPLE IV

Preparation of
N,N'-Thio-bis-(4-dimethylaminoethyleneimino-3-methylphenyl methylcarbamate)

To a solution of 7.13 grams (0.04 m) of 4-dimethylaminomethyleneimino-3-methylphenol and 3.68 grams (0.02 m) of bis-(N-methyl-N-fluorocarbonylamino)sulfide in 50 ml of toluene was added 4.05 grams (0.04 m) of triethylamine. The reaction mixture was heated to 50° C. for 4 hours and then allowed to stand at ambient temperature for 16 hours. Continued heating for additional 5 hours at 50° C. On cooling the mixture was washed with dilute sodium hydroxide solution followed by a water wash until neutral. It was dried over magnesium sulfate and concentrated to an amber colored oil. On addition of ethylether and cooling 4.5 grams of N,N'-Thio-bis-(4-dimethylaminomethyleneimino-3-methylphenyl methylcarbamate) was obtained as a white solid. m.p. 159°–161° C.

Calc'd for $C_{24}H_{32}N_6O_4S$: C, 57.58; H, 6.44; N, 16.79. Found: C, 57.04; H, 6.33; N, 16.40.

EXAMPLE V

Preparation of N,N'-Thio-bis-(4-dimethylaminomethyleneimino-3-methylphenyl methylcarbamate) hydrochloride A solution of 1.9 grams on N,N'-thio-bis-(4-dimethylaminomethyleneimino-3-methylphenyl methylcarbamate) in 25 ml dry methanol was cooled to 10° C. and saturated with hydrochloric acid. The solution was concentrated under reduced pressure. On addition isopropylether it afforded 2.0 grams of N,N'-Thio-bis-(4-dimethylaminomethyleneimino-3-methylphenyl methylcarbamate hydrochloride as a white solid. m.p. 205°–207° C.

Calc'd for $C_{24}H_{34}Cl_2N_6O_4S$: C, 50.26; H, 5.97; N, 14.6. Found: C, 51.11; H, 6.57; N, 14.69.

EXAMPLE VI

Preparation of N-[1-Naphthyl methylcarbamate] N-[2-propargyloxy phenyl methyl carbamate] sulfide To a solution of 4.79 g (0.015 m) of 2-propargyloxy-[N-methyl-N-(N'-methyl-N'-fluorocarbonylaminosulfenyl) carbamoyloxy] benzene and 2.16 g (0.015 m) of 1-naphthol in 50 ml of toluene was added with stirring 1.52 g (0.015 m) of triethylamine. After stirring for 24 hours at room temperature, the reaction mixture was washed successively with water, dilute sodium hydroxide and water until the washings were neutral. The organic layer was dried and concentrated. Chromatographic purification afforded 1.1 g of N-[1-Naphthyl methylcarbamate] N-[2-propargyloxy phenyl methylcarbamate] sulfide as an oil. $N_D^{22}=1.5610$.

Calculated for $C_{23}H_{20}N_2O_5S$: C, 63.29; H, 4.62; N, 6.42. Found: C, 62.29; H, 4.63; N, 6.27.

EXAMPLE VII

Preparation of N-[1-Naphthylmethylcarbamate] N-[4-nonylphenyl methylcarbamate]sulfide To a solution of 15.4 g (0.04 m) of 1-[N-methyl-N-(N'-fluorocarbonyl-N'-methylaminosulfenyl)carbamoyloxy]-4-nonyl benzene and 5.8 g (0.04 m) of 1-naphthol in 300 ml of toluene was added dropwise with stirring 4.1 g (0.04 m) of triethylamine. The reaction mixture was stirred at 60° C. for 20 hrs. On cooling the mixture was washed with water. The organic layer was dried over anhydrous magnesium sulfate and concentrated under reduced pressure to a residual viscous oil. The crude oil was redissolved in n-hexane and purified by passing through a one-inch layer of silica gel. Concentration of the hexane solution afforded 19.0 g of the N-[1-Naphthylmethylcarbamate] N-[4-nonylphenyl methylcarbamate] sulfide as an oil.

Calc'd for $C_{29}H_{36}N_2O_4S$: C, 68.47; H, 7.13; N, 5.50. Found: C, 68.51; H, 7.19; N, 5.61.

EXAMPLE VIII

PREPARATION OF N-[1-NAPHTHYLMETHYLCARBAMATE] N-[4-DODECYLPHENYL METHYLCARBAMATE] SULFIDE

To a solution of 10.0 g (0.032 m) of 1-[N-Methyl-N-)N'-fluorocarbonyl-N'-methylaminosulfenyl) carbamoyloxy] naphthalene and 8.39 g (0.032 m) of 4-dodecylphenol in 100 ml of toluene was added dropwise with stirring 3.24 g (0.032 m) of triethylamine. The reaction mixture was stirred at room temperature for 96 hours and at 50° C. for 16 hours. The reaction mixture was washed with dilute aqueous sodium carbamate and with water until the wash was neutral. The organic layer was dried over anhydrous magnesium sulfate and concentrated under reduced pressure to a residual oil to afford 18.0 g of viscous oil which was purified by passing through a short column of silica gel. $n_D^{22} = 1.5450$.

Calcd. for $C_{32}H_{42}N_2O_4S$: C, 69.78; H, 7.68; N, 5.08. Found: C, 69.35; H, 7.56, N, 4.89.

The compounds of Examples IX–XVII were prepared by the procedures of Examples I–VIII. The physical properties of these compounds are set forth in TABLE I below.

TABLE I

ELEMENTAL ANALYSIS AND PHYSICAL PROPERTIES $$R_1OC(O)-N(CH_3)-S-N(CH_3)-C(O)OR_2$$

| EXAMPLE | R₁ | R₂ | MP° C. | Carbon (calc/found) | Hydrogen (calc/found) | Nitrogen (calc/found) |
|---|---|---|---|---|---|---|
| IX | 2,2-dimethyl-2,3-dihydrobenzofuran-7-yl | benzo[1,3]dithiol-2-yl (2-methylphenyl with dithiolane) | oil | 54.52/54.07 | 5.17/5.53 | 5.53/5.17 |
| X | 2-(propargyloxy)phenyl (OCH₂C≡CH) | 2-(propargyloxy)phenyl (OCH₂C≡CH) | 117–120 | 59.99/59.02 | 4.58/4.53 | 6.53/6.58 |
| XI | 2-methoxy-4-allylphenyl (OCH₃, CH₂CH=CH₂) | 2-methoxy-4-allylphenyl (OCH₃, CH₂CH=CH₂) | 145–146 | 61.00/60.87 | 5.97/5.88 | 5.93/5.93 |
| XII | 2-isopropyl-4-(acetamido)phenyl (CH(CH₃)₂, HNCOCH₃) | 2-isopropyl-4-(acetamido)phenyl (CH(CH₃)₂, HNCOCH₃) | 144–145 | 55.50/55.21 | 6.09/6.02 | 9.96/9.85 |
| XIII | benzo[1,3]dithiol-2-yl | benzo[1,3]dithiol-2-yl | oil | 48.86/46.66 | 4.47/4.24 | 5.18/4.82 |
| XIV | 4-phenoxyphenyl | 4-phenoxyphenyl | 96–98 | 65.10/64.35 | 4.68/4.51 | 5.42/5.59 |
| XV | 3,5-dimethyl-4-(dimethylaminomethyleneamino)phenyl (N=CH—N(CH₃)₂) | 3,5-dimethyl-4-(dimethylaminomethyleneamino)phenyl (N=CH—N(CH₃)₂) | 159–161 | 57.58/57.04 | 6.44/6.33 | 16.79/16.40 |
| XVI | 3,5-dimethyl-4-(dimethylammoniomethyleneamino)phenyl N=CH—⁺NH(CH₃)₂ Cl⁻ | 3,5-dimethyl-4-(dimethylammoniomethyleneamino)phenyl N=CH—⁺NH(CH₃)₂ Cl⁻ | 208–210 | 50.26/51.11 | 5.97/6.57 | 14.65/14.69 |

TABLE I-continued

ELEMENTAL ANALYSIS AND PHYSICAL PROPERTIES $$R_1OC(=O)-N(CH_3)-S-N(CH_3)-COR_2(=O)$$

| EXAMPLE | R₁ | R₂ | MP° C. | ELEMENTAL ANALYSIS (calculated/found) | | |
|---------|----|----|--------|---------------------------------------|---|---|
| | | | | Carbon | Hydrogen | Nitrogen |
| XVII | 4-methyl-2-(H₃C)-phenyl-N=CH—$\overset{+}{N}$H(CH₃)₂ · ½(COO)₂⁻² | 4-methyl-2-(H₃C)-phenyl-N=CH—$\overset{+}{N}$H(CH₃)₂ · ½(COO)₂⁻² | 140–150 (decomposed) | 51.30/51.16 | 5.96/5.69 | 13.81/13.58 |

Selected species of the new compounds were evaluated to determine their pesticidal activity against nematodes, mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°–70° F. and 50–70 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (*Prodenia eridania*, (Cram.)), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.) reared according to the specifications of the Chemical Specialties Manufacturing Association (Blue Book, McNair-Dorland Co., N.Y. 1954; pages 243-244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a soufflé cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

Mite Foliage Spray Test

Adults and nymphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

The results of these tests are set forth in Table I below. In these tests the pesticidal activity of the compounds against aphid, mite, Southern Armyworm, Bean Beetle and house fly was rated as follows:
A = excellent control
B = partial control
C = no control
Dashes indicate no test conducted.

Certain of these compositions were also evaluated to determine their peroral toxicity to mammals. The animal selected for this experiment was the rat. The test results obtained are expressed in terms of the number of milligrams of compositions per kilogram of weight of the animal required to achieve a mortality rate of 50 percent ($LD_{50}$).

POST-EMERGENT HERBICIDAL TEST

Experiments were also conducted to determine the phytotoxicity of representative compositions with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the solutions to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

The results of these experiments are summarized and set forth in Table I, below.

TABLE II
BIOLOGICAL ACTIVITY $$R_1O-\underset{\underset{O}{\|}}{C}-\underset{\underset{CH_3}{|}}{N}-S-\underset{\underset{N}{|}\ CH_3}{N}-\underset{\underset{O}{\|}}{C}-OR_2$$

BIOLOGICAL DATA

| R1 | R2 | Pesticidal Activity | | | | | Phytotoxicity | | | | |
|---|---|---|---|---|---|---|---|---|---|---|---|
| | | Aphid | Mite | Southern Armyworm | Mexican Bean Beetle | Housefly | Bean | Corn | Tomato | Cotton | Soybean |
| 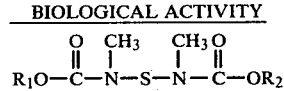 | 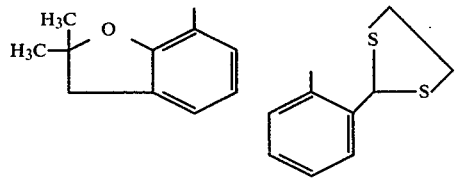 | A | B | A | A | A | 1 | 1 | 1 | 1 | 1 |

TABLE II-continued

BIOLOGICAL ACTIVITY $$R_1O-\overset{O}{\underset{H}{C}}-N-\overset{CH_3}{\underset{|}{S}}-N-\overset{CH_3}{\underset{|}{C}}\overset{O}{\underset{||}{-}}OR_2$$

BIOLOGICAL DATA

| R₁ | R₂ | Pesticidal Activity | | | | Phytotoxicity | | | | | |
|---|---|---|---|---|---|---|---|---|---|---|---|
| | | Aphid | Mite | Southern Army-worm | Mexican Bean Beetle | House-fly | Bean | Corn | To-mato | Cotton | Soy-bean |
| 1-naphthyl | 2-(OCH₂C≡CH)phenyl | A | C | A | A | A | 1 | 1 | 1 | 1 | 2 |
| 2-(OCH₂C=CH)phenyl | 2-(OCH₂C≡CH)phenyl | C | C | A | A | A | — | — | — | — | — |
| 2-OCH₃-4-(CH₂CH=CH₂)phenyl | 2-OCH₃-4-(CH₂CH=CH₂)phenyl | C | C | C | C | C | 1 | 1 | 1 | 1 | 1 |
| 2-CH(CH₃)₂-4-(HNCOCH₃)phenyl | 2-CH(CH₃)₂-4-(HNCOCH₃)phenyl | C | C | A | A | C | 1 | 1 | 1 | 1 | 1 |
| 2-(1,3-dithiolan-2-yl)phenyl | 2-(1,3-dithiolan-2-yl)phenyl | A | C | A | A | A | 1 | 1 | 1 | 1 | 1 |
| 4-phenoxyphenyl | 4-phenoxyphenyl | C | C | C | C | C | 1 | 1 | 1 | 1 | 1 |
| 2-CH₃-4-(N=CH—N(CH₃)₂)phenyl | 2-CH₃-4-(N=CHN(CH₃)₂)phenyl | A | A | A | A | A | 1 | 1 | 1 | 1 | 1 |
| 2-CH₃-4-(N=CH—⁺NH(CH₃)₂)phenyl °Cl⁻ | 2-CH₃-4-(N=CH—⁺NH(CH₃)₂)phenyl °Cl⁻ | A | A | A | A | A | 2 | 1 | 1 | 1 | 2 |
| 2-CH₃-4-(N=CH—⁺NH(CH₃)₂)phenyl ½(°COO)₂²⁻ | 2-CH₃-4-(N=CH—⊕NH(CH₃)₂)phenyl ½(°COO)₂⁻² | A | A | A | A | A | 1 | 1 | 1 | 1 | 2 |
| 1-naphthyl | 4-C₉H₁₉-phenyl | C | C | A | A | C | 1 | 1 | 1 | 1 | 1 |

TABLE II-continued

BIOLOGICAL ACTIVITY $$R_1O-\overset{O}{\underset{\|}{C}}-\overset{CH_3}{\underset{|}{N}}-S-\overset{CH_3}{\underset{|}{N}}-\overset{O}{\underset{\|}{C}}-OR_2$$

BIOLOGICAL DATA

| R₁ | R₂ | Pesticidal Activity | | | | | Phytotoxicity | | | | |
|---|---|---|---|---|---|---|---|---|---|---|---|
| | | Aphid | Mite | Southern Army-worm | Mexican Bean Beetle | House-fly | Bean | Corn | To-mato | Cotton | Soy-bean |
|  | 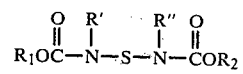 | C | C | A | A | C | 1 | 1 | 1 | 1 | 1 |

The results set forth in TABLE II clearly show the broad spectrum pesticidal activity of the compounds of this invention, as well as their reduced mammalian toxicity and phytotoxicity. It will be understood that the insect, mite and nematode species employed in the above tests are merely representative of a wide variety of pests that can be controlled through the use of the compounds of this invention.

The compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pound of active toxicant per acre.

The pesticides contemplated herein prevent attack by insects, nematodes and mites upon plants or other material to which the pesticides are applied, and they have relatively high residual toxicity. With respect to plants they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds.

What is claimed is:

1. A compound of the formula:

$$R_1O\overset{O}{\underset{\|}{C}}-\overset{R'}{\underset{|}{N}}-S-\overset{R''}{\underset{|}{N}}-\overset{O}{\underset{\|}{C}}OR_2$$

wherein:

R' and R'' are the same or different and are alkyl having from 1 to 4 carbon atoms;

R₁ is:

(A) naphthyl, tetrahydronaphthyl, benzofuranyl, benzodioxanyl, dihydrobenzofuranyl, indanyl, benzothienyl or benzodioxanlanyl, all of which may be either unsubstituted or substituted with one or more alkyl groups; or (B) phenyl, either unsubstituted or substituted with one or more alkyl, alkoxy, alkylthio, dialkylaminomethyleneimino, dialkylamino, methylenedioxy, halo, nitro, cyano, alkynyloxy, phenoxy, alkenyl, alkynyl, dialkylformamidino, alkylthioalkyl, alkylsulfonylalkyl, alkylsulfinylalkyl, alkoxycarbonylamino, trihalomethyl, 2-dioxalanyl, 2-dioxanyl, 2-dithianyl, 2-dithiolanyl or 2-oxathiolanyl group;

R₂ is either substituted or unsubstituted alkylphenyl having from 9 to 20 aliphatic carbon atoms, wherein the permissible substituents are one or more alkynyloxy, alkynyl, phenoxy, alkenyl, alkoxycarbonylamino, trihalomethyl, alkylthioalkyl, alkylsulfonylalkyl, alkylthioalkyl, cyano, dialkylformamidino, dialkylaminomethyleneimino, methylenedioxy, dicyanoethenylene, 2-dithianyl, 2-dioxalanyl, 2-dioxanyl, 2-oxathiolanyl or 2-dithiolanyl groups;

with the proviso that $R_1$ and $R_2$ substituents individually may not include more than eight aliphatic carbon atoms and with the proviso that when $R_1$ is substituted or unsubstituted dihydrobenzofuranyl, $R_2$ is other than alkylphenyl or alkylphenyl substituted with alkylthioalkyl, alkylsulfonylalkyl or alkylsulfinylalkyl.

2. A claim according to claim 1 wherein R' and R" are methyl.

3. A compound according to claim 1 wherein $R_1$ is naphthyl, or phenyl substituted with one or more alkoxy, alkyl, phenoxy, alkenyl, alkynyloxy, 2-dithiolanyl, 2-oxathiolanyl, 2-dithianyl, alkylthio, halo, dialkylamino, alkoxycarbonylamino or dialkylformamidino groups.

4. A compound according to claim 1 wherein $R_2$ is alkylphenyl having from 9 to 16 aliphatic atoms.

5. A compound according to claim 1 wherein:
R' and R" are methyl;
$R_1$ is naphthyl or phenyl substituted with one or more alkoxy, alkyl, phenoxy, alkenyl, alkynyloxy, 2-oxathiolanyl, 2-dithiolanyl, 2-dithianyl, alkylthio, halo, dialkylamino, alkoxycarbonylamino or dialkylformamidino groups; and
$R_2$ is alkylphenyl having from 9 to 16 aliphatic carbon atoms.

6. A compound according to claim 5 wherein $R_2$ is para nonylphenyl.

7. N-[1-Naphthylmethylcarbamate] N-[4-nonylphenyl methylcarbamate] sulfide.

8. An insecticidal and nematocidal composition comprising an acceptable carrier and as the active toxicant an insecticidally or nematocidally effective amount of a compound according to claim 1.

9. An insecticidal and nematocidal composition comprising an acceptable carrier and as the active toxicant an insecticidally or nematocidally effective amount of a compound according to claim 2.

10. An insecticidal and nematocidal composition comprising an acceptable carrier and as the active toxicant an insecticidally or nematocidally effective amount of a compound according to claim 3.

11. An insecticidal and nematocidal composition comprising an acceptable carrier and as the active toxicant an insecticidally or nematocidally effective amount of a compound according to claim 4.

12. An insecticidal and nematocidal composition comprising an acceptable carrier and as the active toxicant an insecticidally or nematocidally effective amount of a compound according to claim 5.

13. An insecticidal and nematocidal composition comprising an acceptable carrier and as the active toxicant an insecticidally or nematocidally effective amount of a compound according to claim 6.

14. An insecticidal and nematocidal composition comprising an acceptable carrier and as the active toxicant an insecticidally or nematocidally effective amount of a compound according to claim 7.

15. A method of controlling insects and nematodes which comprises subjecting them to an insecticidally or nematocidally effective amount of a compound according to claim 1.

16. A method of controlling insects and nematodes which comprises subjecting them to an insecticidally or nematocidally effective amount of a compound according to claim 2.

17. A method of controlling insects and nematodes which comprises subjecting them to an insecticidally or nematocidally effective amount of a compound according to claim 3.

18. A method of controlling insects and nematodes which comprises subjecting them to an insecticidally or nematocidally effective amount of a compound according to claim 4.

19. A method of controlling insects and nematodes which comprises subjecting them to an insecticidally or nematocidally effective amount of a compound according to claim 5.

20. A method of controlling insects and nematodes which comprises subjecting them to an insecticidally or nematocidally effective amount of a compound according to claim 6.

21. A method of controlling insects and nematodes which comprises subjecting them to an insecticidally or nematocidally effective amount of a compound according to claim 7.

* * * * *